United States Patent [19]

Adair

[11] Patent Number: 5,792,045
[45] Date of Patent: Aug. 11, 1998

[54] STERILE SURGICAL COUPLER AND DRAPE

[76] Inventor: Edwin L. Adair, 317 Paragon Way, Castle Pines Village, Colo. 80104

[21] Appl. No.: 609,954

[22] Filed: Mar. 4, 1996

Related U.S. Application Data

[63] Continuation-in-part of Ser. No. 317,199, Oct. 3, 1994, Pat. No. 5,498,230, and Ser. No. 350,682, Dec. 7, 1994, Pat. No. 5,591,119.

[51] Int. Cl.$^6$ ............................................................ A61B 1/04
[52] U.S. Cl. ............................................. 600/125; 600/122
[58] Field of Search ............................... 600/121–125, 600/174, 112

[56] References Cited

U.S. PATENT DOCUMENTS

| Re. 34,002 | 7/1992 | Adair . | |
|---|---|---|---|
| 2,537,303 | 1/1951 | Cobb, Jr. et al. . | |
| 4,318,395 | 3/1982 | Tawara . | |
| 4,522,196 | 6/1985 | Cunningham et al. . | |
| 4,756,304 | 7/1988 | Watanabe . | |
| 4,844,071 | 7/1989 | Chen et al. . | |
| 5,198,894 | 3/1993 | Hicks . | |
| 5,205,280 | 4/1993 | Dennison, Jr. et al. . | |
| 5,239,981 | 8/1993 | Anapliotis . | |
| 5,274,500 | 12/1993 | Dunn . | |
| 5,301,657 | 4/1994 | Lafferty et al. | 600/112 X |
| 5,458,132 | 10/1995 | Yabe et al. | 600/121 |
| 5,496,259 | 3/1996 | Perkins | 600/124 |

FOREIGN PATENT DOCUMENTS

| 0 437 004 A2 | 7/1991 | European Pat. Off. ......... A61B 19/00 |
|---|---|---|
| 91300555 | 7/1992 | European Pat. Off. . |
| 93116113 | 4/1994 | European Pat. Off. . |
| 8914215 U | 2/1991 | Germany . |

*Primary Examiner*—John P. Leubecker
*Attorney, Agent, or Firm*—Fields and Johnson P.C.

[57] ABSTRACT

An apparatus and method are provided for enclosing a non-sterile camera setup comprising a video camera, its trailing cables, and a standard optical connector for use of the unsterile camera setup in the sterile environment of an operating room. The apparatus includes a coupler having a first end for attachment to the unsterile camera setup and a second end for attachment to a sterile endoscope. A passageway is formed inside the coupler that extends from the first end to the second end thereof providing an optical pathway whereby an image from the endoscope may be transmitted to the unsterile camera setup. A transparent window is mounted transversely across the passageway between the first and second ends of the coupler providing a sterile barrier therebetween. In operation, a sterile drape is positioned over the first end of the coupler and extends over the unsterile camera setup. The sterile drape is secured between the first and second ends of the coupler by a locking ring which secures the distal end of the drape so that a fluid and airtight seal is formed therebetween. A sterile disposable wand may be releasably attached to the second end of the coupler for providing support to the unsterile camera setup as it is attached to the coupler. The wand may then be detached enabling connection of the sterile endoscope to the second end of the coupler.

24 Claims, 14 Drawing Sheets

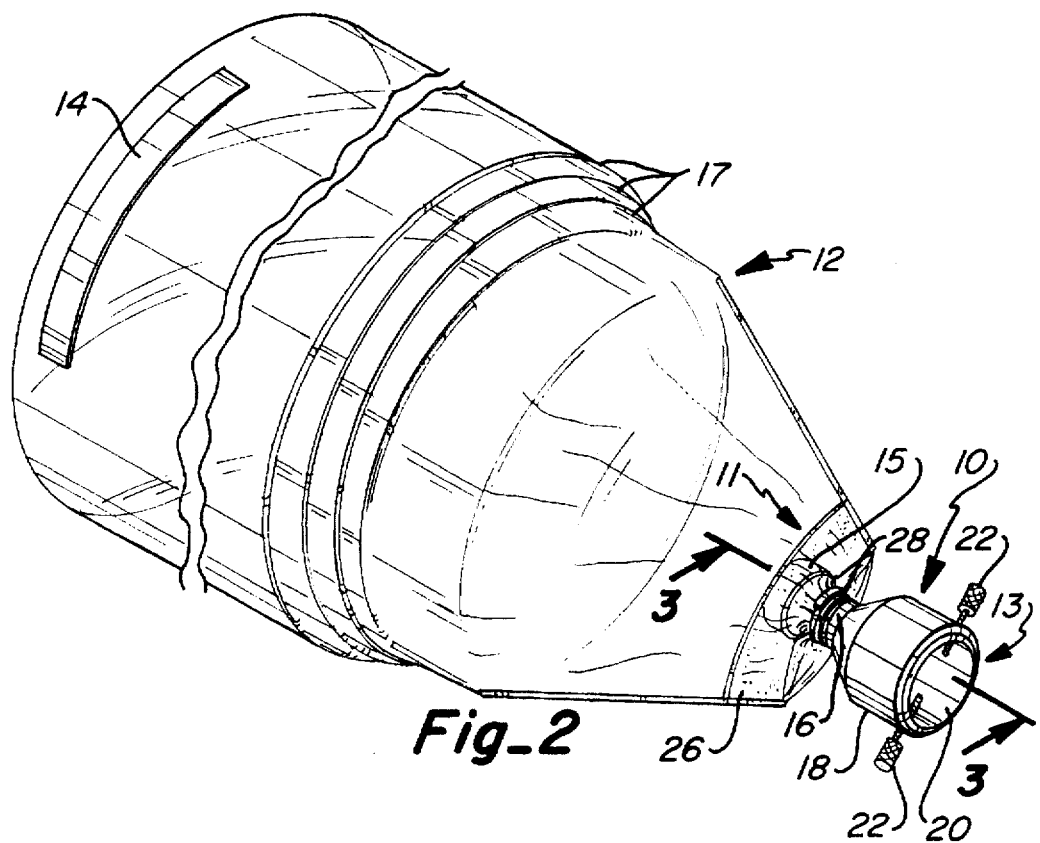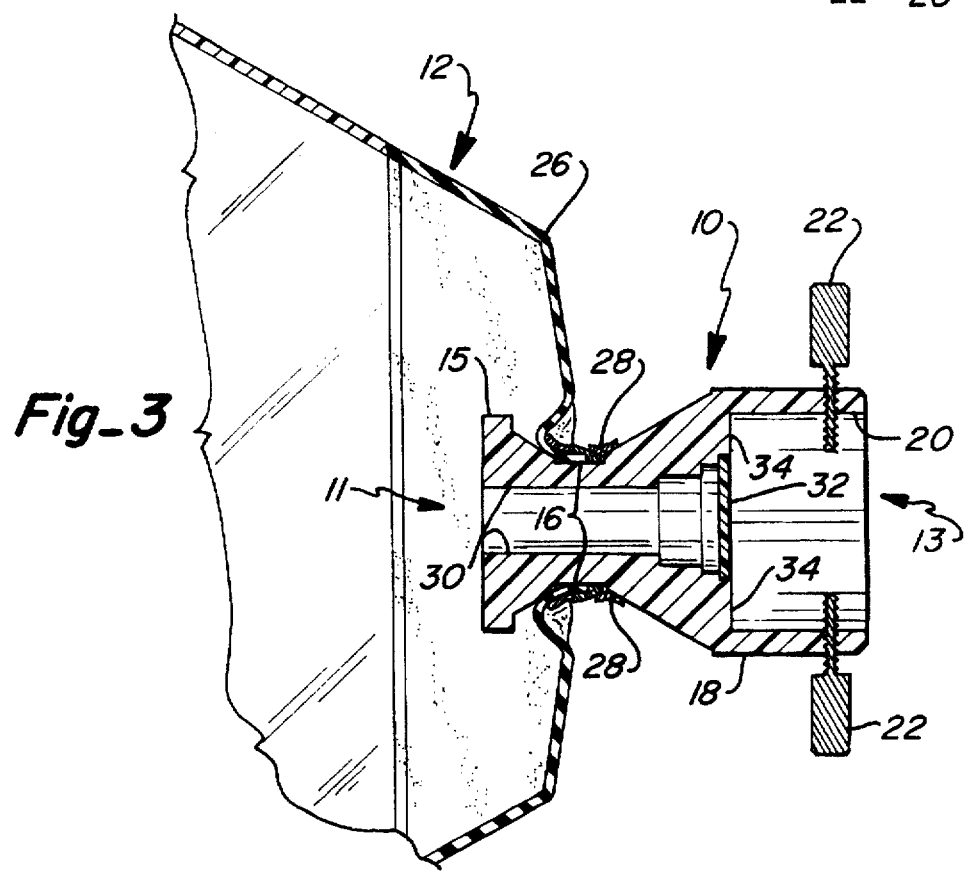

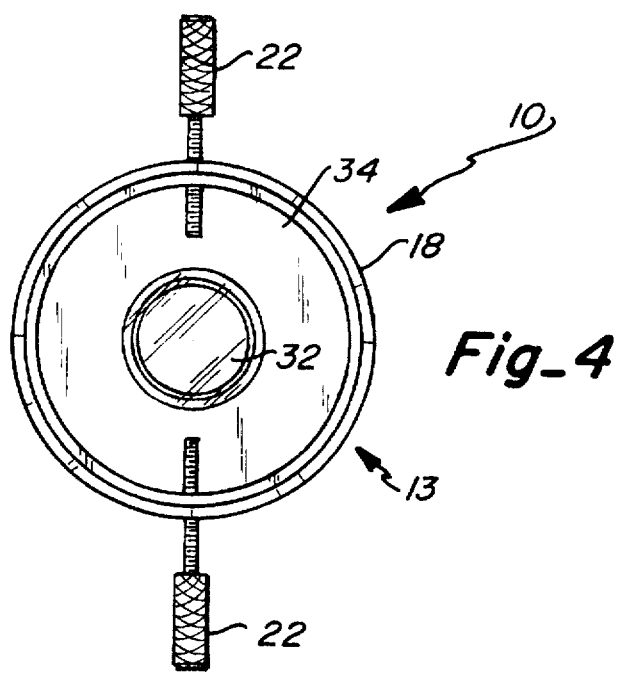
Fig_4
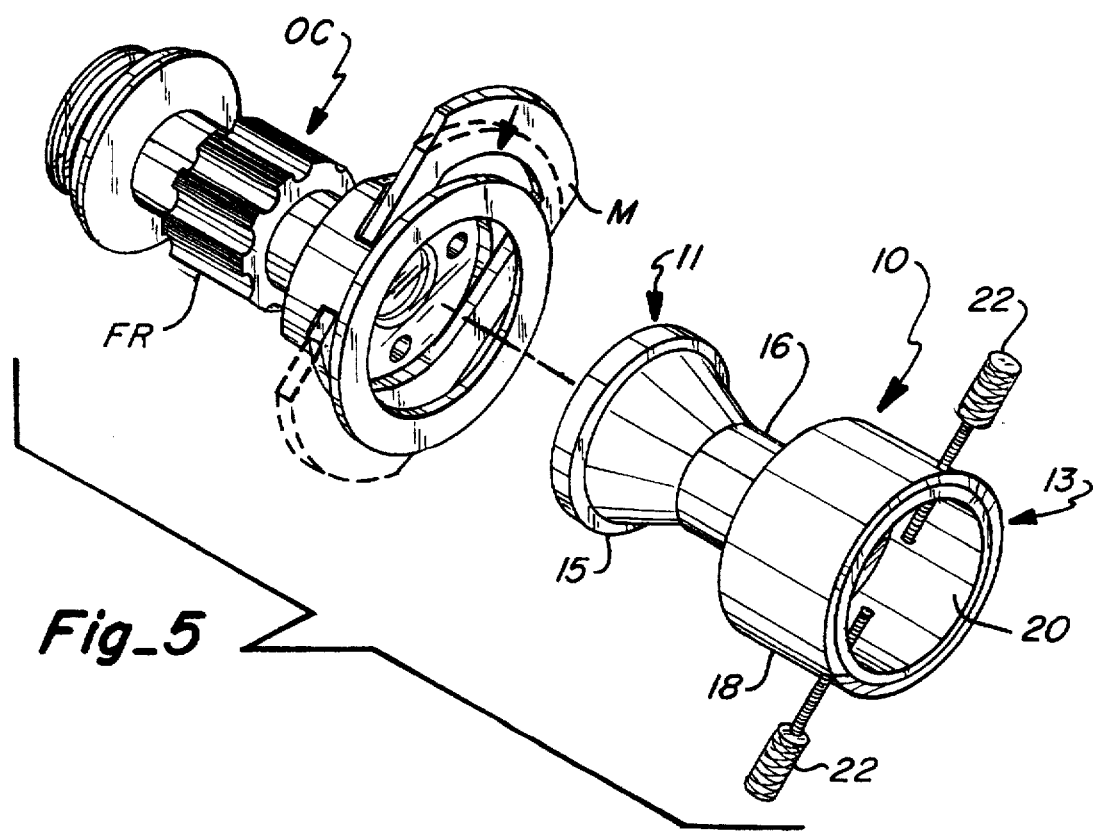
Fig_5

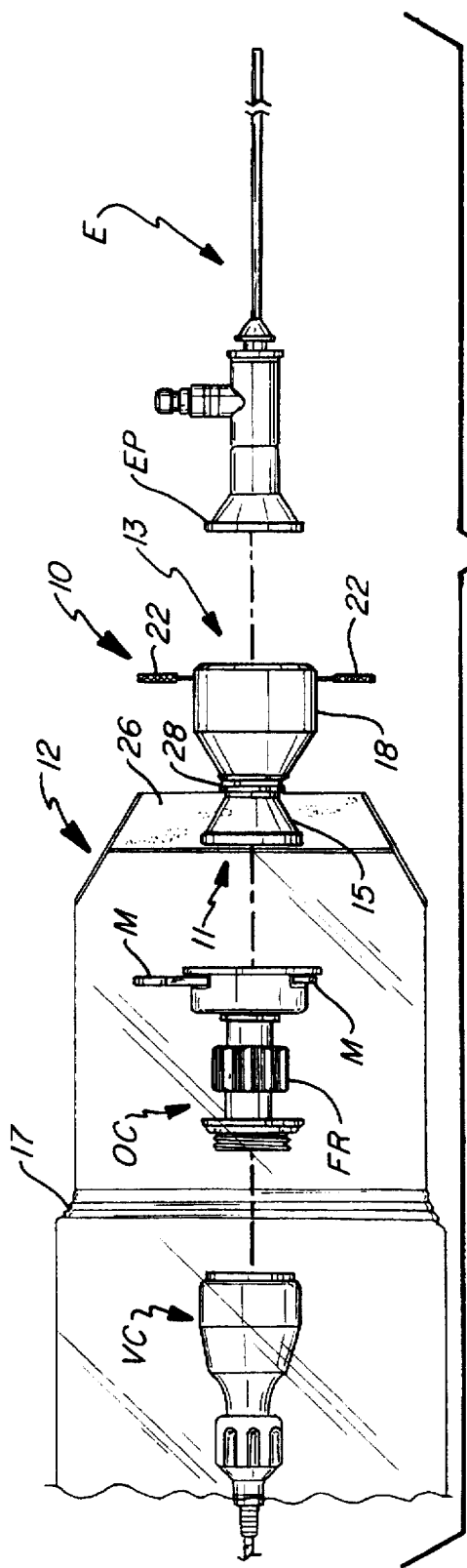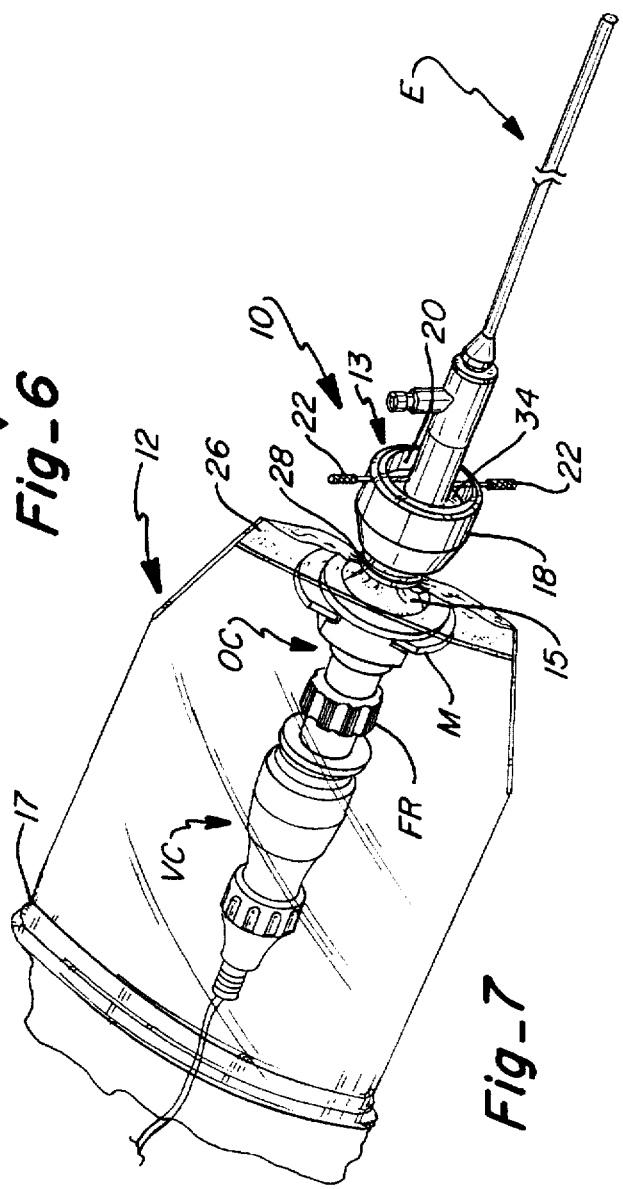

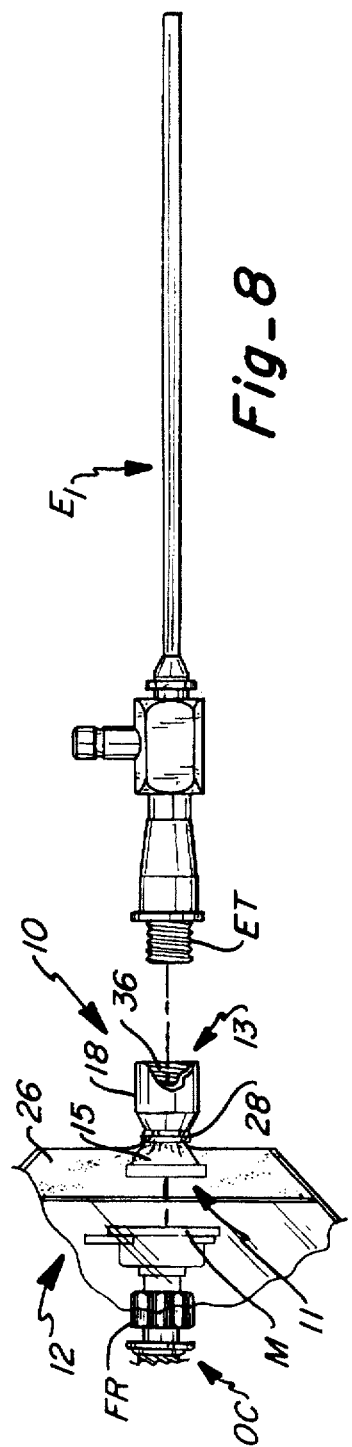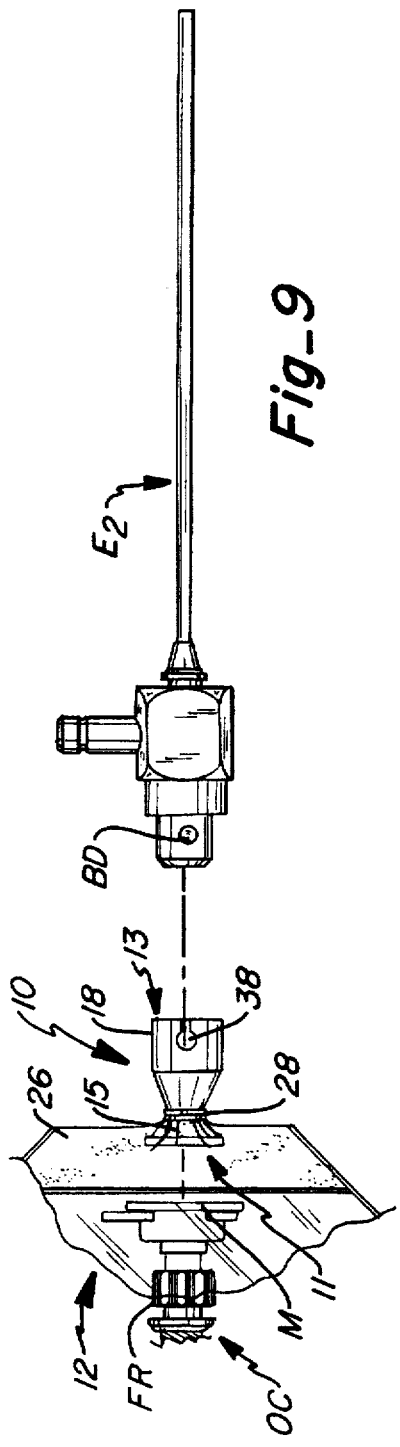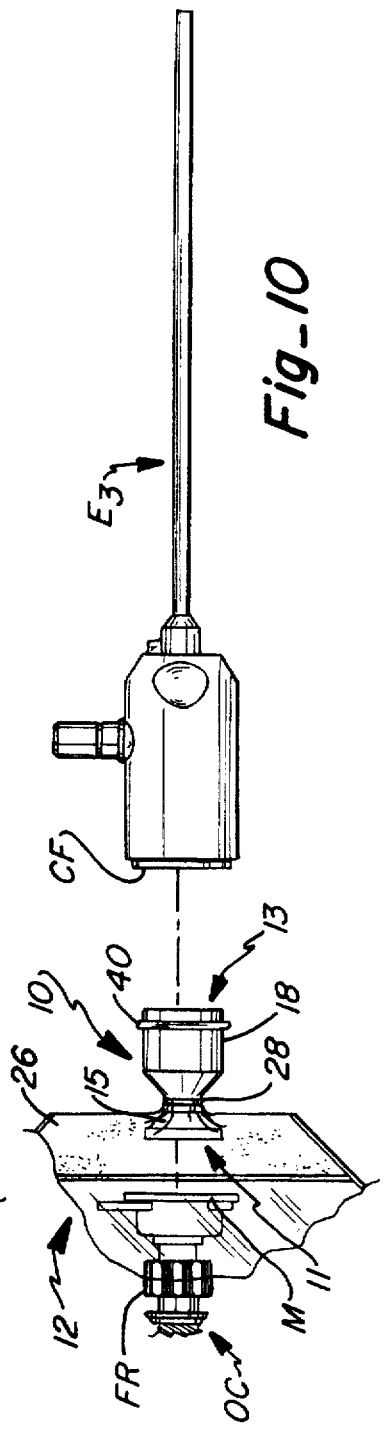

STERILE SURGICAL COUPLER AND DRAPE

TECHNICAL FIELD

This application is a continuation-in-part of Adair U.S. Ser. No. 08/317,199, filed Oct. 3, 1994 entitled "Sterile Connector and Video Camera Cover for Sterile Endoscope", now U.S. Pat. No. 5,498,230 and a continuation-in-part of Adair U.S. Ser. No. 08/350,682, filed Dec. 7, 1994 entitled "Sterile Surgical Coupler and Drape now U.S. Pat. No. 5,591,119."

This invention relates to a sterile surgical coupler and drape for use in the sterile environment of an operating room. More particularly, the invention relates to such a coupler and drape which encloses an unsterile camera setup including a camera and an optical connector wherein the unsterile optical connector attaches to a first end of the coupler and a second end of the coupler in turn attaches to a sterile endoscope.

BACKGROUND ART

For many years, unsterile surgical cameras and optical connectors known in the art as "C" or "V" mount connectors have been used in surgery by placing them into a sterile plastic bag or drape that has a distal end including an opening for receiving the eyepiece of a sterile or disinfected endoscope. The act of coupling the sterile or disinfected endoscope through the opening in the drape to the unsterile optical connector can create contamination. That is, the interior of the drape that houses the unsterile camera and optical connector is exposed to the sterile environment of an operating room through the hole located at the distal end of the drape. When the eyepiece of the endoscope is inserted through this hole for connection to the optical connector, this hole often becomes enlarged thus enhancing the possibility of contamination traveling from the interior of the drape to the sterile operating room. The further acts of aligning the endoscope with the optical connector and sealing the distal end of the drape around the protruding distal portion of the endoscope can also result in further contamination.

My earlier U.S. Pat. No. Re. 34,002 discloses a sterilizable video camera cover which has a connector including a guideway for receiving an unsterile video camera within it in a predetermined fixed orientation. One end of the video camera cover receives a sterile mount and endoscope in a fixed position with respect to the camera. An accordion-folded sleeve is positioned on the camera cover and is extended over the trailing cables of the camera to maintain the sterile environment within the operating room even though the camera and trailing cables are unsterile.

A sterile pouch for containing a standard still picture camera for use in an operating room is shown in U.S. Pat. No. 2,537,303 to Cobb, Jr. et al. However, there is no thought in this device of connecting the camera to other optical means. Other containers for protecting cameras in varying environments are shown in U.S. Pat. No. 3,026,784 to Byers, U.S. Pat. No. 3,821,759 to Vooght and U.S. Pat. No. 2,132,549 to Wenstrom. However, none of these references are intended for use in an operating room to maintain the environment within the operating room in a sterile condition when the camera is not sterile.

There are numerous references which disclose sterile drapes or covers for isolating an unsterile camera and its trailing cables from the sterile environment of an operating room. Examples of such references include U.S. Pat. No. 5,274,500 to Dunn, U.S. Pat. No. 5,078,483 to Herzberg, U.S. Pat. No. 5,198,894 to Hicks, and U.S. Pat. No. 5,325,846 to Szabo. While each of these references may be adequate for their intended purpose, none of these references disclose a device which allows endoscopes to be freely interchanged with a single camera setup and yet maintain the required sterility of an operating room.

DISCLOSURE OF THE INVENTION

An apparatus and method is provided for enclosing a non-sterile video camera, its trailing cables, and a standard optical connector such as a "C" mount connector for use of the camera in the sterile environment of an operating room. In a first preferred embodiment, the apparatus includes a coupler having a first end for attachment to the unsterile optical connector and a second end for attachment to a sterile endoscope. A passageway is formed inside the coupler that extends from the first end to the second end providing an optical pathway whereby an image from the endoscope may be transmitted to the camera. A transparent window is mounted transversely across the passageway between the first and second ends of the coupler which provides a sterile barrier therebetween. A sterile drape is positioned over the first end of the coupler and is secured to a neck portion that joins the first and second ends of the coupler. The sterile drape is secured such that a fluid and airtight seal is formed between the ends of the coupler. Typically, the seal is formed by surgical tape, adhesive, a wire drape ring, or by a Teflon® seal. The first end of the coupler includes an annular mounting that may resemble the eyepiece of a standard endoscope. This annular mounting is compatible with common optical connectors available from various manufacturers, including Olympus, Karl Storz and others. The second end of the coupler may include a number of embodiments which are intended to allow this end of the coupler to be attached to differing types of endoscopes. For example, in one embodiment, the second end of the coupler includes a cylindrical interior wall for receiving a standard endoscope with an annular eyepiece. Means are provided for securing the endoscope to the second end of the coupler, such as by retaining screws, pins, or other appropriate means. In another form of the first embodiment, the second end of the coupler may include an interior wall having threads which engage with an endoscope having an exterior threaded end instead of the conventional eyepiece. In another form of the first embodiment, the second end of the coupler may include a generally circular recess for receiving an endoscope of the type which has a spring-loaded ball detent. In yet another form of the first embodiment, the second end of the coupler may include an external O-ring for receiving an endoscope of the type having a compression fitting.

In a second preferred embodiment, the second end of the coupler may include a sliding quick release for attachment to the eyepiece of an endoscope. The sliding quick release mechanism is similar to the sliding quick release mechanisms found on many types of optical connectors.

In a third preferred embodiment, the coupler may be comprised of two parts wherein an optical coupler part is prepositioned within the drape and the endoscope coupler part is then attached to the optical coupler part. Having a coupler comprising two parts in some uses makes the coupler easier to use than a coupler having only one integral structure. For the second and third embodiments, in order to effectively seal the drape to the coupler, a locking ring may be used which captures the drape either between the two parts of the two part coupler or between the optical connector and the coupler.

In a fourth preferred embodiment, the coupler may include two parts, namely, an endoscope mount portion and an optical connector mount portion. The fourth embodiment differs from the third embodiment in that the optical connector mount functions similarly to the optical coupler part and locking ring.

The drape may be accordion folded or roll folded so to accommodate the desired packaging configuration prior to use. Conveniently, the drape may also include a pull tab for extending the drape for use. The coupler and drape are generally sterilized by gamma radiation or by gas sterilization and thus may be completely sterile.

According to another novel aspect of this invention, a sterile disposable wand is provided to aide in the attachment of the video camera and optical connector to the coupler. The sterile disposable wand is removably attached to the second end of the coupler prior to connecting the second end with an endoscope. In operation, once the optical connector is attached to the first end of the coupler, the wand can be removed and the endoscope can be coupled to the second end of the coupler.

Stated in another way in broader terms, the invention is a sterile system for coupling a sterile endoscope to an unsterile camera wherein endoscopes are freely interchangeable with the same camera setup so that sterility can be maintained. A coupling means is provided for coupling an unsterile optical connector to a sterile endoscope. The coupling means may be any suitable device having a first end for receiving the unsterile optical connector and a second end for receiving the sterile endoscope. A drape is provided wherein the first end of the coupler remains completely sealed from the sterile environment of the operating room while the second end of the coupler is exposed to the operating room and which allows one to attach the needed endoscope without having to access the optical connector or camera. The sterile drape completely encloses the camera, its trailing cables, and the optical connector. The sterile wand is convenient for stabilizing the video camera and optical connector as they are attached in line to the coupler.

Some video cameras and optical connectors may be partially disinfected by soaking or heating, however, it is quite difficult to completely sterilize these pieces of equipment without incurring tremendous expense due to the cost of labor and equipment associated with surgical sterilization techniques. Thus, a preferred method of endoscopy is one in which unsterile cameras and accessories may be coupled to sterile endoscopes with operating room sterility maintained throughout. With the invention just described, it is possible to use a standard and unsterile surgical video camera and a standard and unsterile optical connector such as a "C" mount connector with a multitude of different types of endoscopes. As described, sterility can be maintained throughout any acts of endoscope manipulation such as changing or adjusting an endoscope with the same camera setup.

Additional advantages of this invention will become apparent from the description which follows, taken in conjunction with the accompanying drawings.

BRIEF DESCRIPTION OF THE DRAWINGS

FIG. 2 is a perspective view of a sterile surgical coupler and drape constructed in accordance with a first preferred embodiment of this invention;

FIG. 3 is a longitudinal cross-sectional view taken along line 3—3 of FIG. 2 showing the interior details of the coupler and drape;

FIG. 4 is an end view of the first preferred embodiment of the coupler illustrating the coupler having an internal optical pathway therethrough;

FIG. 5 is a perspective exploded view of the first preferred embodiment wherein the coupler is detached from the drape and a standard optical connector prior to engagement of the coupler with the optical connector;

FIG. 6 is an exploded side view of the first preferred embodiment illustrating the alignment of a camera, optical connector and an endoscope prior to connection;

FIG. 7 is a perspective view of the first preferred embodiment illustrating the invention in use wherein an unsterile camera and optical connector are inserted within the drape and connected to the first end of the coupler, and a sterile endoscope is connected to the second end of the coupler;

FIG. 8 is a partial fragmentary exploded side view of the first embodiment illustrating an alternative construction of the second end of the coupler which has interior threads for receiving an endoscope of the type having an exterior threaded end;

FIG. 9 is an exploded side view of the first embodiment illustrating another alternative construction of the second end of the coupler which includes a generally circular recess for receiving an endoscope of the type having a spring-loaded ball detent connection;

FIG. 10 is an exploded side view of the first embodiment illustrating yet another alternative construction of the second end of the coupler which includes an external O-ring for receiving an endoscope of the type having a compression fitting connection;

FIG. 12a is an enlarged fragmentary partial cross-sectional view of the locking ring in FIG. 12, illustrating the use of a spring washer;

FIG. 12b is an enlarged fragmentary partial cross-sectional view of the locking ring in FIG. 12, illustrating the use of a Teflon® seal in lieu of a spring washer;

BEST MODE FOR CARRYING OUT THE INVENTION

Typically, a sterile endoscope is connected by means of an optical connector to a surgical camera. The distal end of the endoscope can be introduced into an internal body sight for viewing. The maintenance of sterility in these types of medical procedures is critical. While there does exist sterile cameras and optical connectors, it is more common in the art to encounter surgical cameras and optical connectors that are unsterile and that are shielded from the sterile environment of the operating room by means of a sterile drape or bag.

Figure 1:
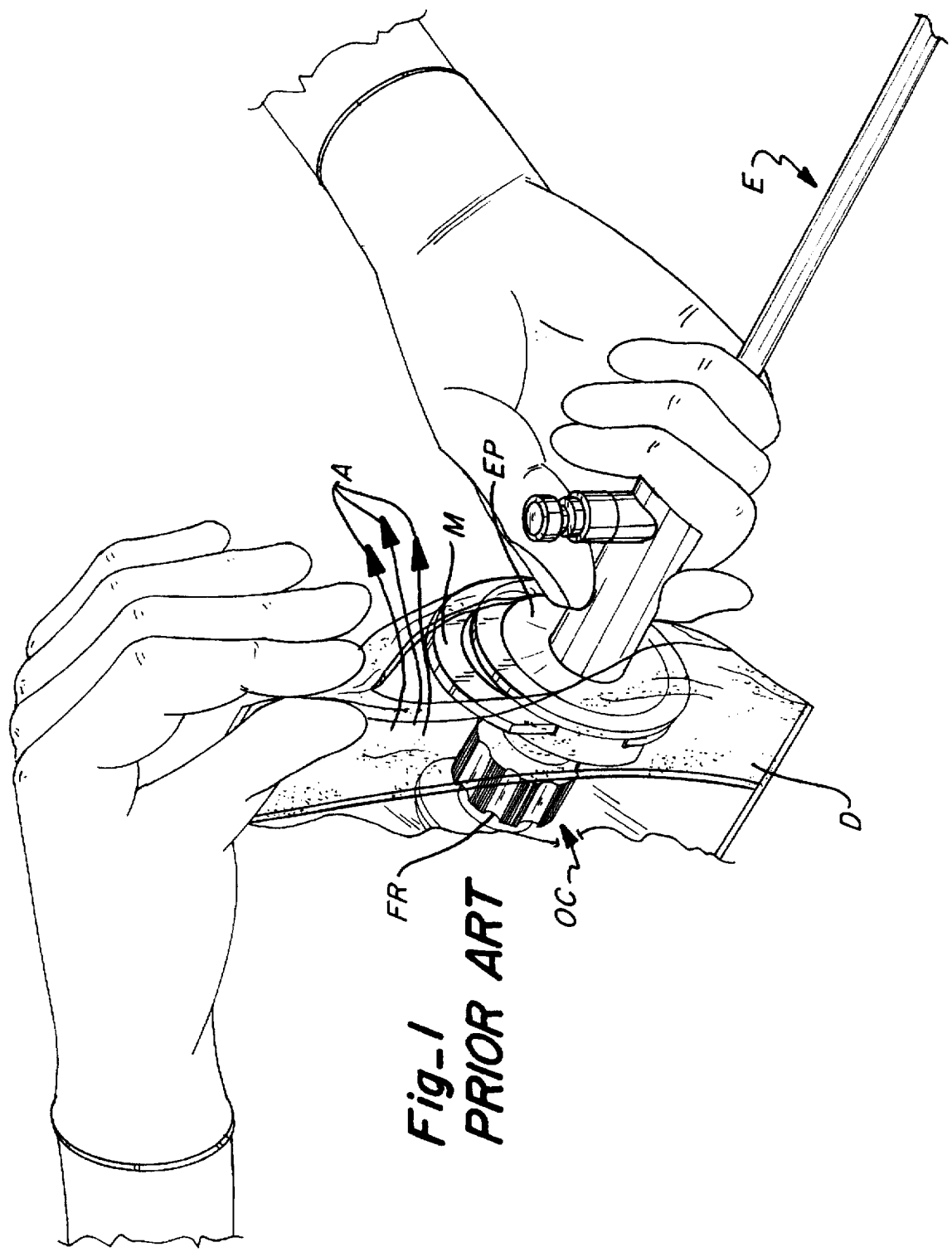
FIG. 1 is a perspective view of the prior art illustrating the eyepiece of a sterile endoscope being directly coupled to an unsterile optical connector wherein the eyepiece is inserted through an opening in the distal end of the drape.

The invention disclosed herein is advantageous over the prior art because sterility can be maintained during endoscopic procedures. In the prior art method and device of FIG. 1, a standard endoscope E with eyepiece EP is inserted within drape D. The act of inserting the eyepiece EP into the drape D and coupling the eyepiece EP to an unsterile mount portion M of optical connector OC allows contamination to travel from the inside of the drape D to the sterile environment of the operating room. This path of contamination is generally shown by arrows A. Further contamination can occur by manipulation of the endoscope to achieve correct camera alignment and by sealing the open distal end of the drape to the protruding distal portion of the endoscope. Assuming the interior of the drape is sterile prior to the insertion of a camera and optical connector, the invention disclosed herein is still advantageous over the prior art. That is, sterility in the prior art can be maintained by first inserting the endoscope through the opening in the distal end of the drape and then sealing the drape with respect to the endoscope prior to introducing the unsterile camera and optical connector into the drape. However, if it were desired then to change the type of endoscope used with the existing camera setup, the sterile barrier between the camera and the distal end of the endoscope would have to be broken by reopening the sealed end of the drape. This act can result in contamination and is therefore an undesirable method of interchanging endoscopes with the same camera setup. As will be discussed, the invention disclosed herein allows endoscopes to be freely interchanged and ensures the maintenance of sterility during endoscope procedures.

In accordance with this invention, in a first preferred embodiment, a disposable sterile coupler 10 and attached sterile drape 12, as best seen in FIGS. 2 and 6, is provided for coupling an unsterile camera setup, comprising an unsterile video camera VC and optical connector OC having a focusing ring FR, to a sterile endoscope E. The overall structure of the sterile coupler 10 and drape 12 can best be seen by viewing FIGS. 2 and 3. The sterile coupler 10 includes a first end 11 having an annular mounting 15 which attaches to a common optical connector such as a "C" mount connector. This annular mounting 15 resembles the eyepiece of a standard endoscope. The coupler 10 further includes a second end 13 having an endoscope mount 18 characterized by a substantially cylindrical shape which may be configured to match the particular type of endoscope used. As best seen in FIGS. 3 and 6, in the first preferred embodiment, the endoscope mount 18 includes an interior cylindrical wall 20 for receiving a standard endoscope E having an annular eyepiece EP. Between the annular mounting 15 and endoscope mount 18 is a neck portion 16. An annular mounting 15 is inserted within an opening located at the distal end 26 of the drape 12 such that the opening surrounds neck portion 16. A sealing means 28 such as surgical tape may be used to seal the distal end 26 against the neck portion 16, thus providing a sterile barrier between the first and second ends of the coupler 10. Sealing and bonding of the drape 12 to the coupler 10 may also be done by a variety of methods, including adhesives, shrink-wrap or double-faced adhesive strips.

Sterile drape 12 may include folds 17 in order to reduce the size of the drape for storage prior to use. As shown in FIG. 2, folds 17 may be telescopic wherein consecutive drape sections are folded on top of one another, or alternatively folds 17 may be folded in a roll configuration (not shown) like a condom. If folds 17 are telescopic, pull tab 14 may be provided in order to extend the drape for use. As seen in FIG. 3, the primary purpose of coupler 10 is to provide an optical pathway and sterile barrier between a sterile endoscope E and an unsterile camera setup including video camera VC and optical connector OC. Accordingly, interior passageway 30 is provided to allow light to be transmitted from the endoscope E to the video camera VC. To maintain sterility, optically clear window 32 is provided which allows the passage of light and provides a sterile barrier between the video camera VC and endoscope E. As best seen in FIGS. 3 and 6, for use of the coupler 10 with an endoscope E of the type having a conventional eyepiece EP, the eyepiece EP is inserted within endoscope mount 18 such that the eyepiece EP is pressed flush against interior wall 34 and window 32. Retaining screws 22 may then be used to secure the eyepiece EP. Alternatively, endoscope mount 18 could be configured like mount portion M of optical connector OC in order to receive the standard eyepiece EP of an endoscope. Other methods of securing the mount 18 to the endoscope are possible within the intended scope of this disclosure as will be discussed below.

In addition to the construction of endoscope mount 18 as illustrated in FIGS. 2 through 7 of the first embodiment, endoscope mount 18 may be configured to match any number of differing types of endoscopes. For example, as shown in FIG. 8, endoscope mount 18 may include interior threads 36 for which to receive exterior threads ET of endoscope $E_1$. As shown in FIG. 9, endoscope mount 18 may include a generally circular recess 38 for which to receive ball detent BD of endoscope $E_2$. In yet another arrangement, as shown in FIG. 10, endoscope mount 18 may include an O-ring 40 for which to receive an endoscope $E_3$ that has a compression fitting CF.

The coupler 10 can be made of a suitable plastic or metal material which is sterilizable by various methods such as gas sterilization or gamma radiation and thus is made completely sterile. A suitable material for the coupler may be polycarbonite or PETG, or possibly acrylic or styrene. Similarly, the sterile drape 12 may be made out of a material such as polyethylene preferably from 1 to 6 mils in thickness, that is sterilizable also making the drape completely sterile.

In use of the first embodiment, as best seen in FIGS. 4–6, video camera VC and optical connector OC are inserted within the proximal end of sterile drape 12. Mounting portion M of optical connector OC is coupled to annular mounting 15 of coupler 10. Video camera VC may then be attached to connector OC. Sterile drape 12 is then pulled back over the optical connector OC, video camera VC and its trailing cables thus providing a sterile covering isolating the unsterile camera setup from the sterile operating environment. Sterile endoscope E may then be coupled with endoscope mount 18 of coupler 10. The endoscope E may be secured by means of retaining screws 22 or other appropriate securing means. If it is desired to use a different type of endoscope having differing optical qualities, retaining screws 22 are simply released and endoscope E is removed from mount 18. A new endoscope may then be introduced wherein sterility is maintained during the change in endoscopes. After use, the optical connector OC and endoscope E are disconnected from the coupler 10, and the drape 12 and coupler 10 are thrown away.

Figure 11:
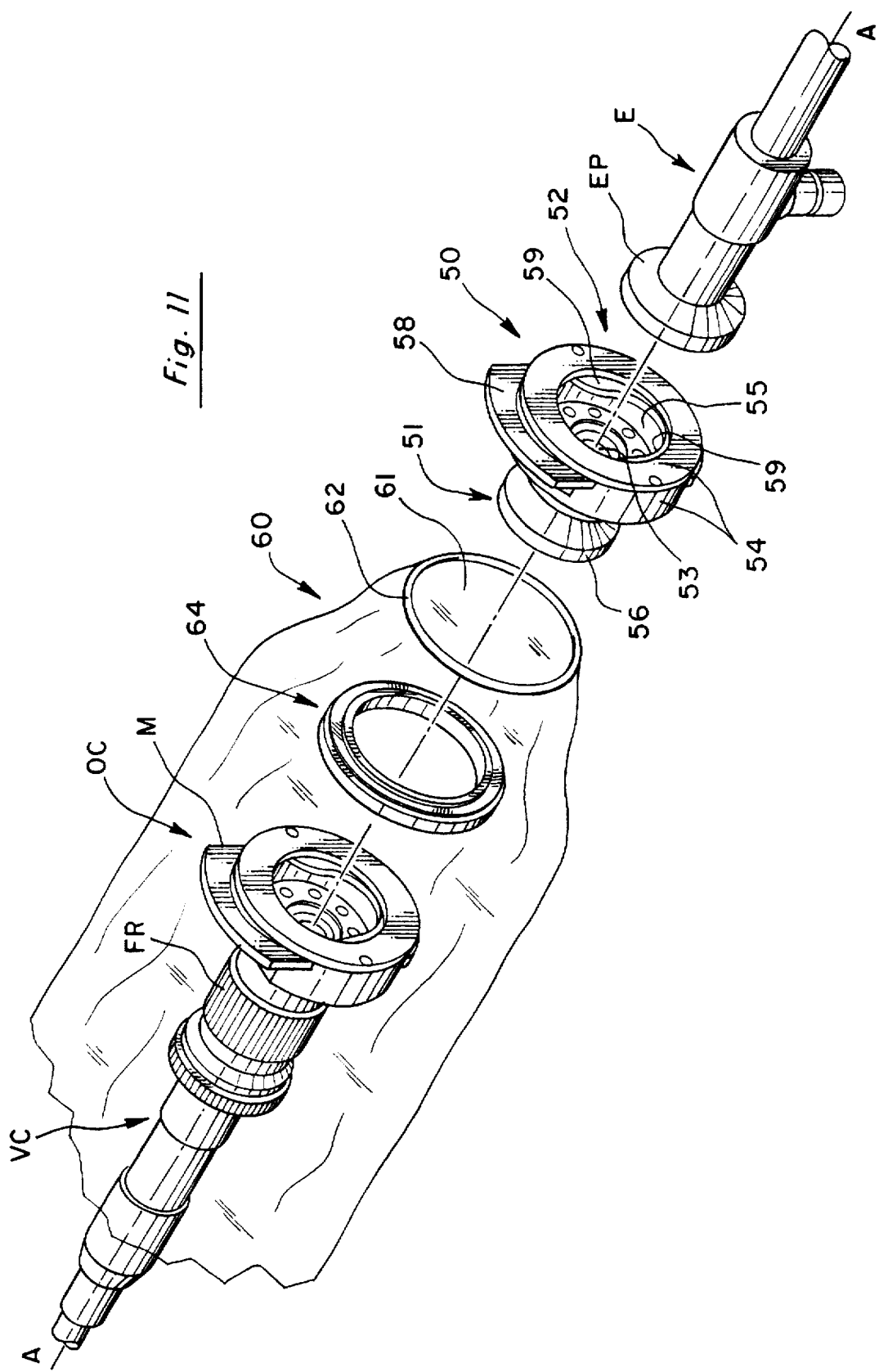
FIG. 11 is a perspective exploded view of a second preferred embodiment of the coupler and drape of this invention illustrating the coupler detached from the drape and optical connector and also detached from the standard endoscope prior to use.
Figure 12:
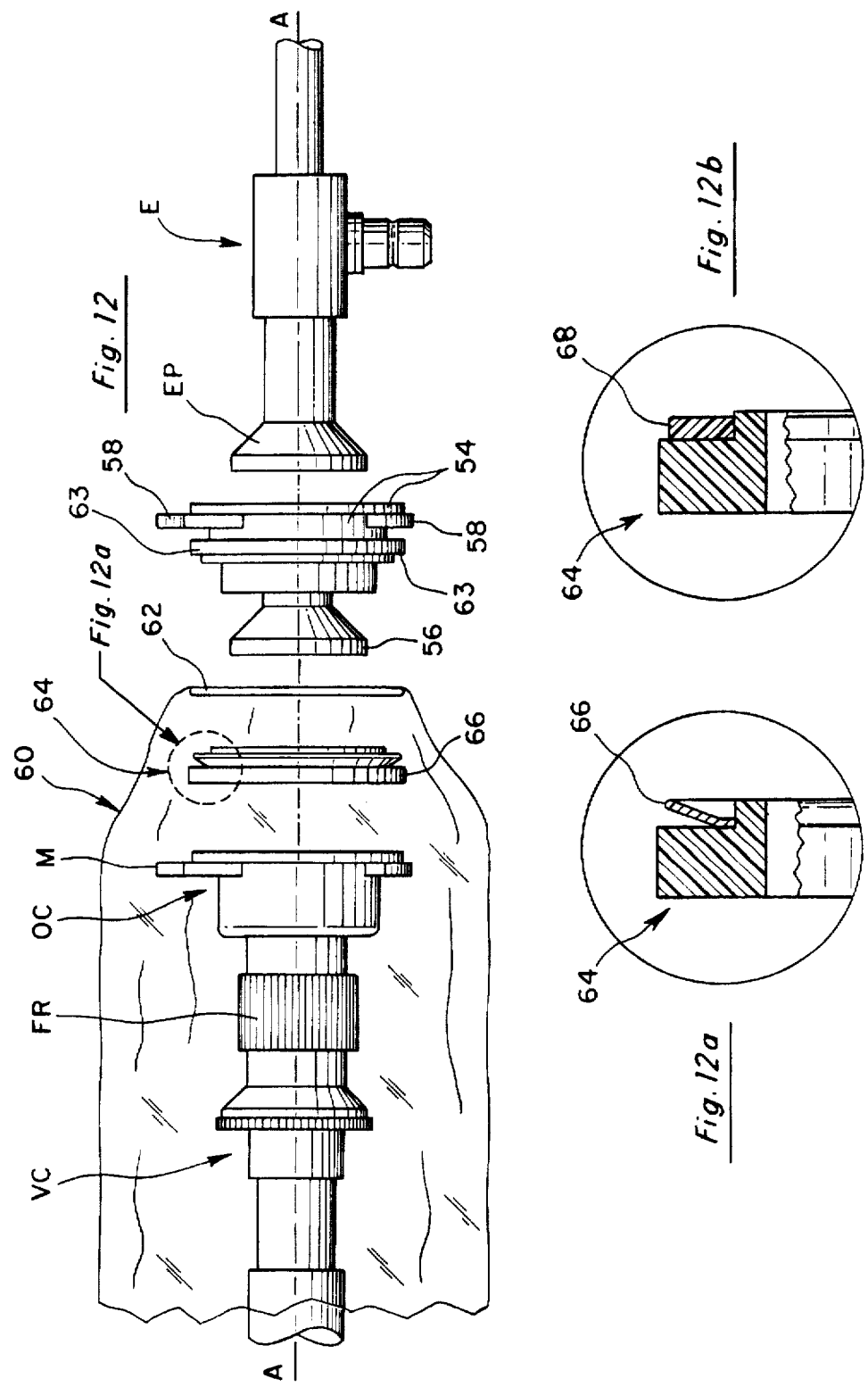
FIG. 12 is an exploded side view of the second preferred embodiment, as shown in FIG. 11, illustrating the alignment of a video camera, optical connector and an endoscope prior to connection.
Figure 13:
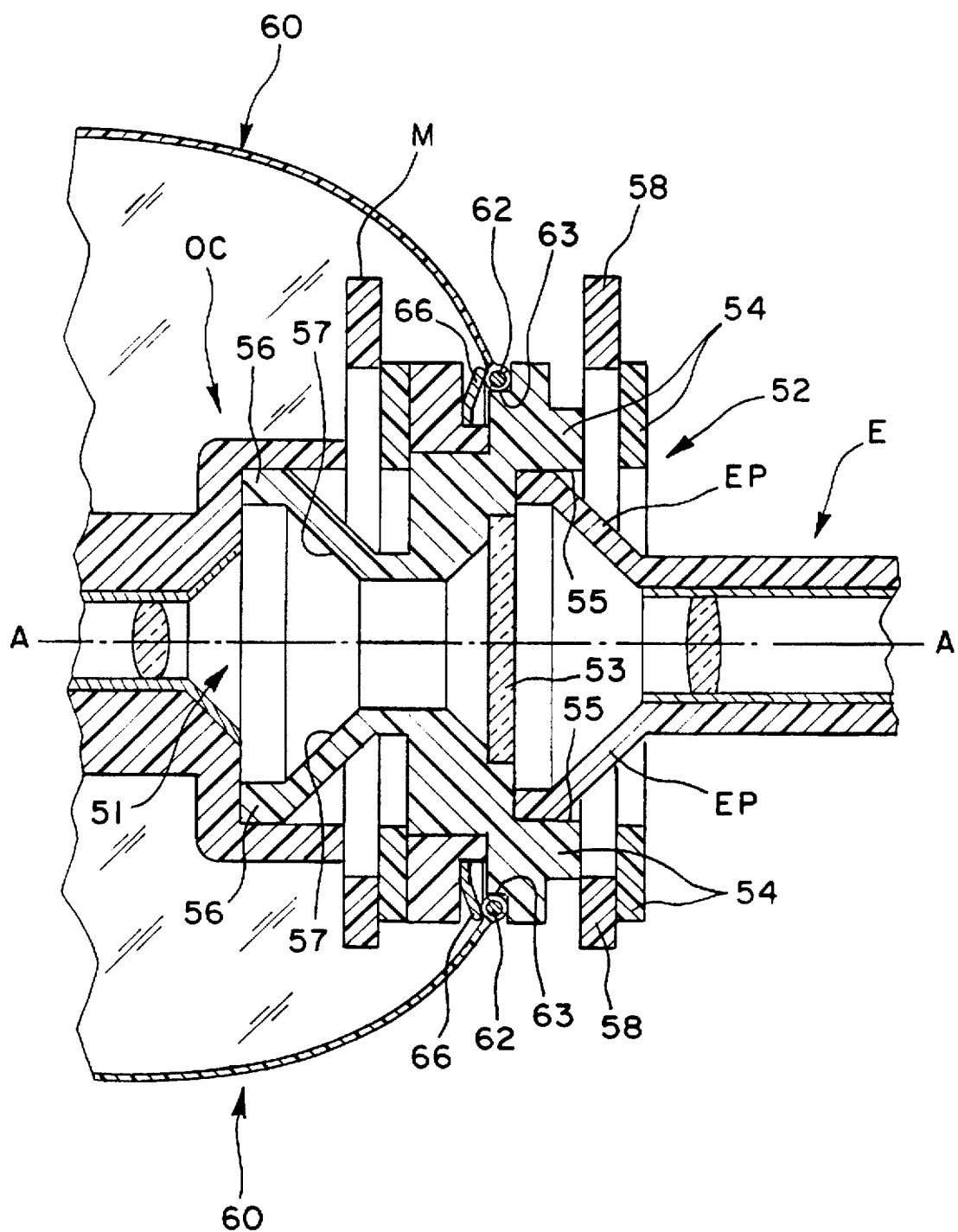
FIG. 13 is a longitudinal cross-sectional view, showing the interior details of the second embodiment of the coupler and drape of this invention when in use with a sterile camera setup including an optical connector and endoscope.

In a second preferred embodiment of the sterile surgical coupler and drape of this invention, a sterile coupler 50 is provided, as best seen in FIGS. 11–13. The sterile coupler 50 includes a first end 51 which attaches to the optical connector OC, and a second end 52 which connects to the endoscope E. As with the first embodiment, a window 53 is positioned within the coupler 50 for providing a sterile barrier between the optical connector OC and the sterile endoscope E. Coupler 50 includes an endoscope mount 54 having an interior passageway 55 which optically communicates with the window 53. Furthermore, the coupler 50 includes an optical coupler mount 56 also including an interior passageway 57 which communicates with the opposite side of window 53. In order to attach the coupler 50 to a desired endoscope E, coupler 50 includes a securing means such as sliding quick release mechanism 58 which is similar to the mount portion M of optical connector OC. Mechanism 58 is mounted transversely with respect to axis A—A which defines the longitudinal direction. In operation, sliding quick release 58 may be depressed to enlarge the opening within interior passageway 57 enabling an endoscope to be inserted therein. Upon relieving pressure on the sliding quick release 58, V portion 59 of quick release 58 then engages the eyepiece EP of the endoscope E. A spring member (not shown) disposed within endoscope mount 54 provides the sliding quick release 58 with spring tension to releasably engage the endoscope E. According to the second embodiment, drape 60 includes a drape ring 62 which may be constructed of a circular shaped wire that is integral with the distal end of the drape. Drape ring 62 defines the drape opening 61. FIG. 11 illustrates the arrangement of the sterile coupler 50 with respect to optical connector OC and locking ring 64 when the drape and coupler of this invention is in use. However, prior to use, the sterile coupler and drape of this invention is packaged such that the sterile drape extends over the second end 52 of the coupler 50 with the locking ring 64 exposed exteriorly of the drape 60. Thus, it will be understood that when in use, the drape 60 is inverted so that it is pulled back over the first end 51 of the coupler 50 and completely over optical connector OC, video camera VC and its trailing cables. As best seen in FIGS. 12a and 13, locking ring 64 may include sealing means such as spring washer 66 to help provide a water and airtight seal for capturing the drape 60 therebetween. More specifically, endoscope mount 54 includes an engagement flange 63 which receives drape ring 62. The contact of washer 66 against drape ring 62 which is pressed against flange 63 ensures a tight seal. In lieu of spring washer 66, as shown in FIG. 12b, a Teflon® seal 68 may be used to provide the liquid and airtight seal.

Figure 14:
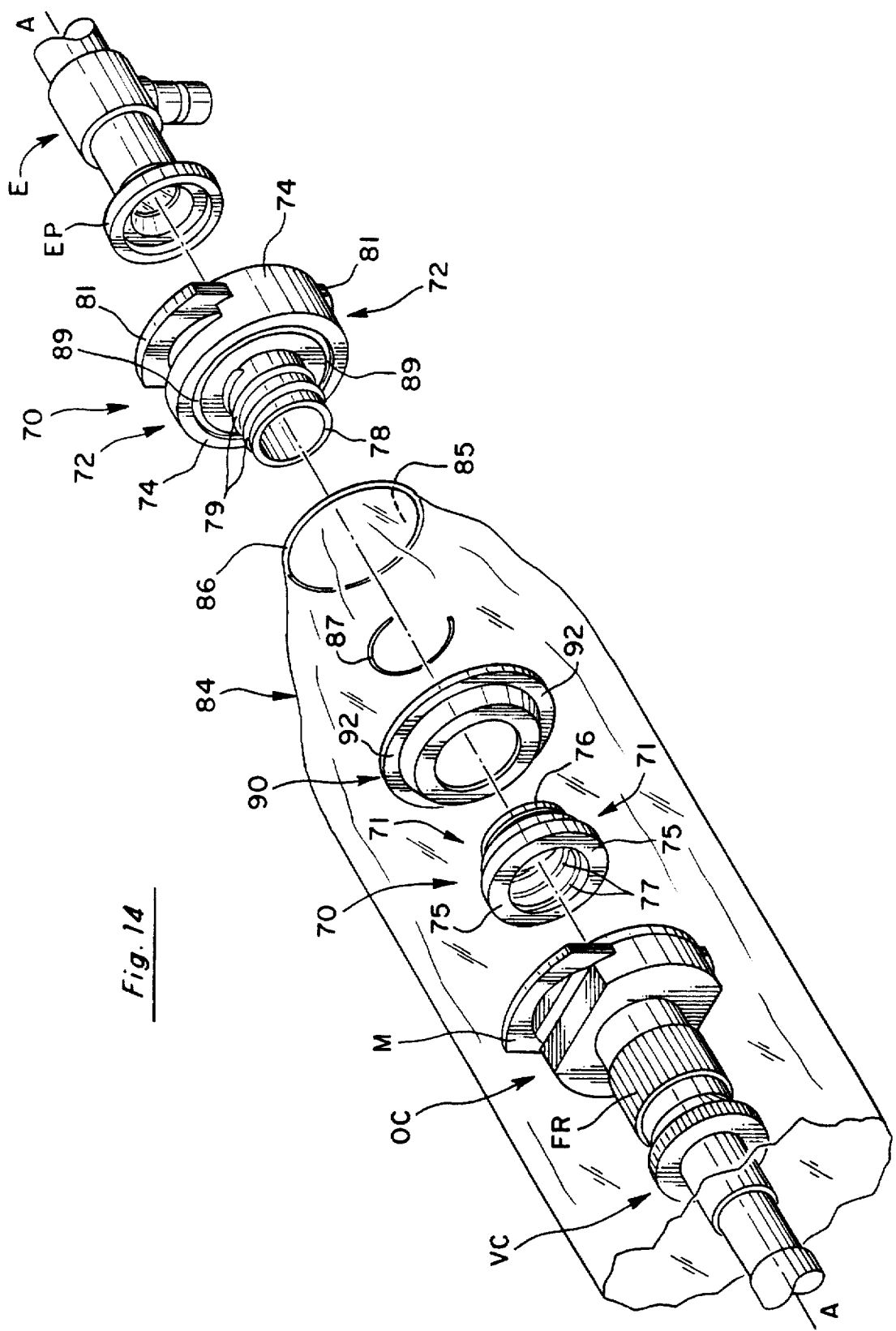
FIG. 14 is a perspective exploded view of a third preferred embodiment of the coupler and drape of this invention illustrating the coupler detached from the drape and optical connector and also detached from a standard endoscope, prior to use.
Figure 15:
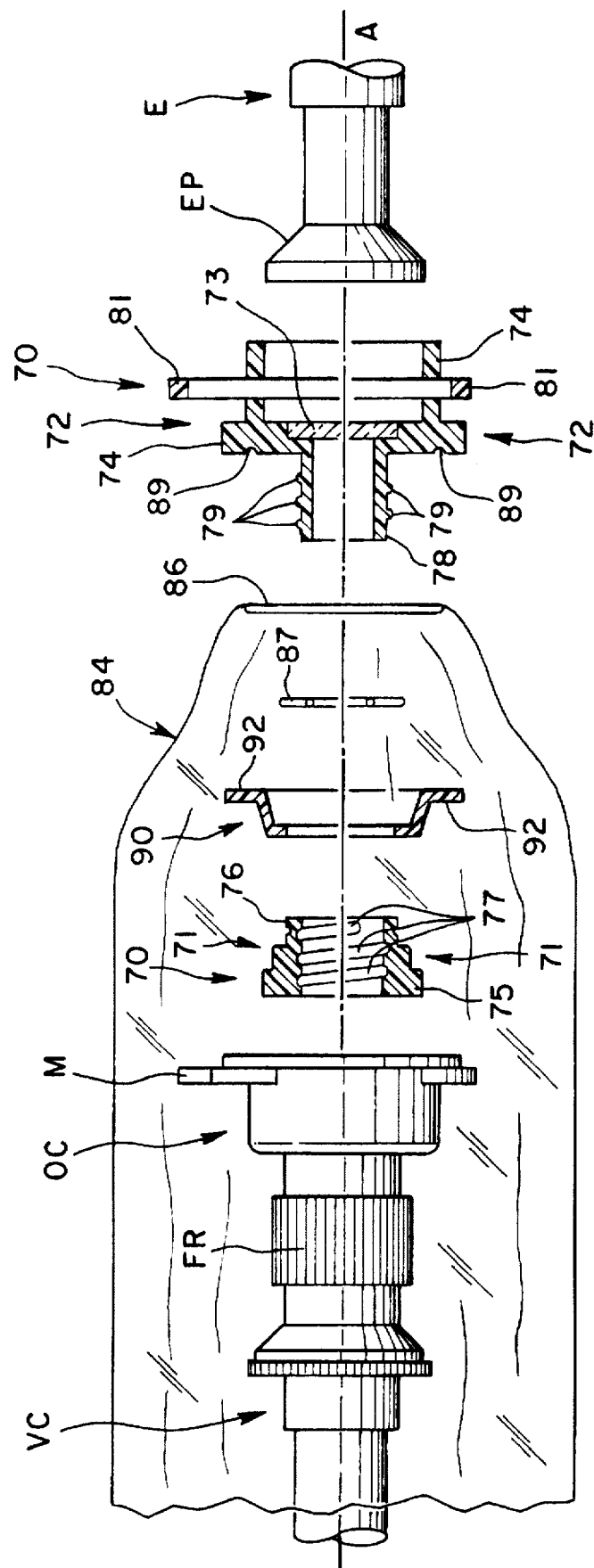
FIG. 15 is an exploded longitudinal cross-sectional side view of the second preferred embodiment of the coupler and drape of this invention illustrating the alignment of a video camera, optical connector, and an endoscope prior to connection.

In a third preferred embodiment of the coupler and drape of this invention, a sterile coupler 70 is provided which comprises two main structural elements, namely, an optical coupler part 71 and an endoscope coupler part 72. This third embodiment is best seen in FIGS. 14 and 15. As with the second embodiment, the positioning of the drape is illustrated as when the drape and coupler are in use in surgery. That is, when packaged, the drape is initially extended over endoscope coupler part 72 but then is reversed and pulled back over optical coupler part 71. Endoscope coupler part 72 includes a window 73 to provide a sterile barrier between the unsterile optical connector OC and video camera VC and the sterile endoscope E. Coupler part 72 further includes endoscope mount 74 and sliding quick release 81 which serves as the structure for attachment to endoscope E. Flange portion 78 of endoscope coupler part 72 includes a plurality of externally exposed threads 79 which mate with internal thread 77 of optical coupler part 71. Optical coupler part 71 includes optical coupler mount 75 which is engaged by the mount portion M of optical connector OC. Internal threaded portion 77 of optical coupler part 71 mates with external threads 79 to provide a positive locking connection. Flange 76 of optical coupler part 71 is insertable through locking ring 90, locking wire 87 and ultimately slides over flange 78 so that threads 79 may engage internal threaded portion 77. Locking ring 90 includes a flange 92 which assists in capturing the drape 84 between ring 90 and coupler part 72. As with the second embodiment, drape 84 includes a drape ring 86 defining a drape opening 85. In order provide a watertight and airtight seal, drape ring 86 engages with groove 89 formed on endoscope mount 74. Locking wire 87 serves to stablize the connection between optical coupler part 71 and locking ring 90.

Figure 16:
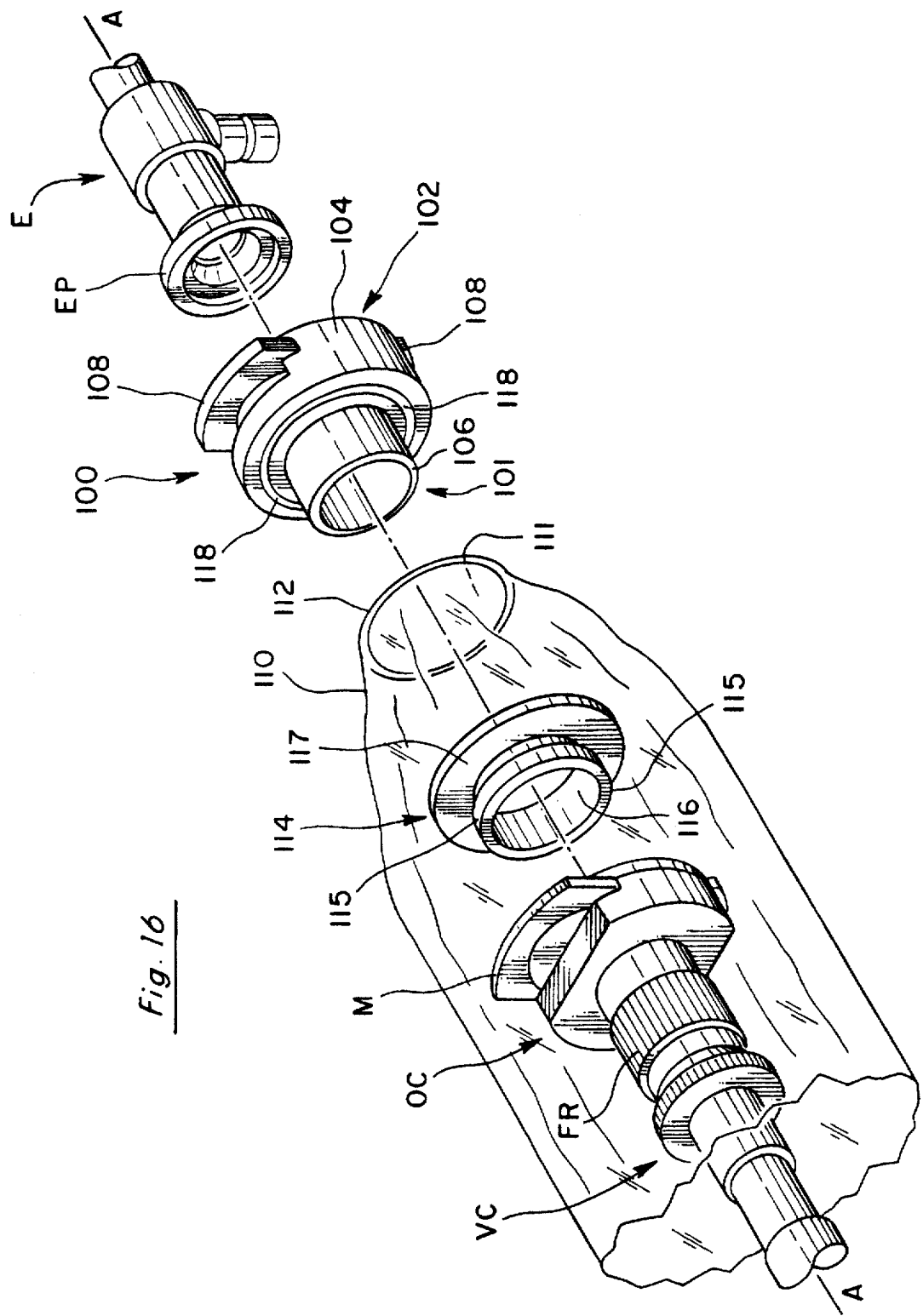
FIG. 16 is a perspective exploded view of a fourth preferred embodiment of the coupler and drape of this invention, wherein the coupler is detached from the drape and optical connector and also detached from a standard endoscope, prior to use.
Figure 17:
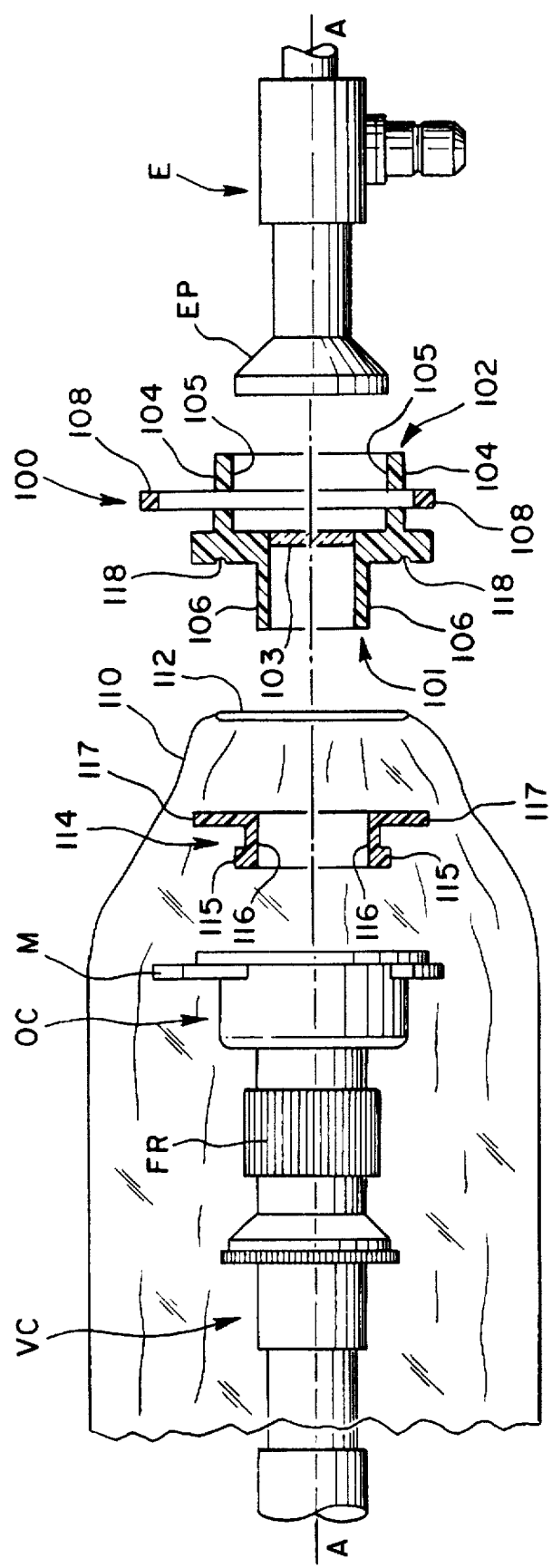
FIG. 17 is an exploded longitudinal cross-sectional side view of the fourth preferred embodiment of the coupler and drape of this invention illustrating the alignment of a video camera, optical connector and endoscope prior to connection.

According to a fourth preferred embodiment of the coupler and drape of this invention, as best seen in FIG. 16 and 17, a sterile coupler 100 is provided. The fourth embodiment is similar to the second embodiment, however in the fourth embodiment, structure corresponding to the optical coupler mount 56 of the second embodiment is made integral with the locking ring 64, as will be explained below. Sterile coupler 100 includes a first end 101 which is engageable with the optical connector OC. Second end 102 is engageable with an endoscope E. A window 103 provides a sterile barrier between the optical connector OC and the endoscope E. Coupler 100 further includes an endoscope mount 104 which attaches to the endoscope E by means of sliding quick release 108. The endoscope E is received within interior passageway 105 wherein V portion (not shown) engages the eyepiece EP of the endoscope E. Mount 104 includes annular flange 106 which has a smooth exterior surface. Drape 110 includes a drape ring 112 defining a drape opening 111. Locking ring 114, functionally corresponding to locking ring 64 of the second embodiment, also includes an optical coupler mount 115 and interior passageway 116 which functionally correspond to optical coupler mount 56 coupler 50. In use, the drape 110 extends over the first end 101 of coupler 100 and locking ring 114 is engaged with annular flange 106 of endoscope mount 104. A close tolerance fit between flange 106 and interior passageway 116 of locking ring 114 provides a positive locking connection. Optical connector OC engages optical coupler mount 115 in the same manner the optical connector OC engages offical coupler mount 56. Flared flange 117 of locking ring 114 provides an enlarged surface area in which to grasp and hold drape 110 between endoscope mount 104 and locking ring 114. Endoscope mount groove 118 provides a matching seat for drape ring 112.

Figure 18:
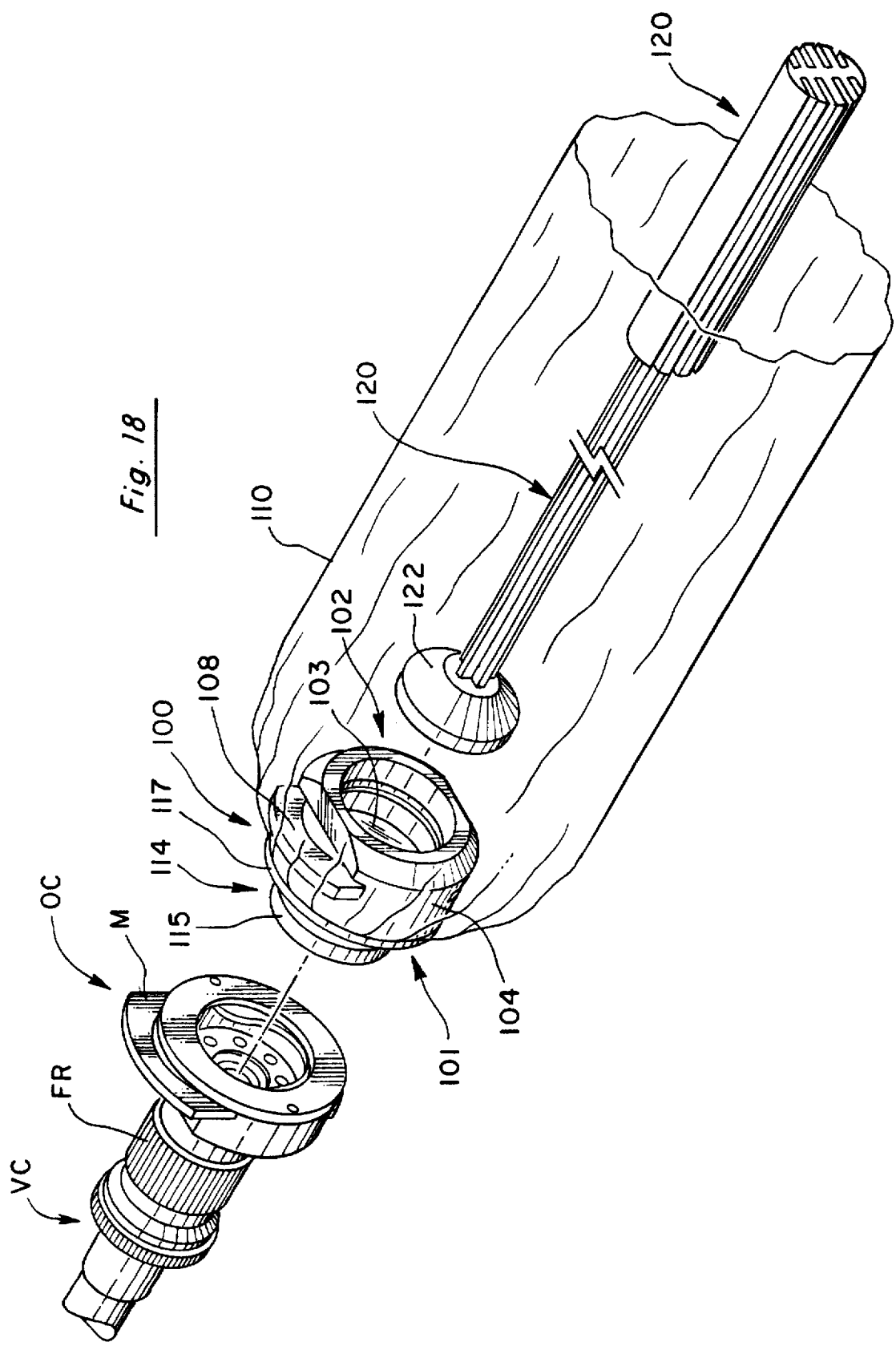
FIG. 18 is a perspective view of the fourth preferred embodiment of the coupler and drape of this invention illustrating the invention as it would be packed prior to use, wherein a sterile disposable wand is connected to the second end of the coupler and the drape is extended over the second end of the coupler.
Figure 19:
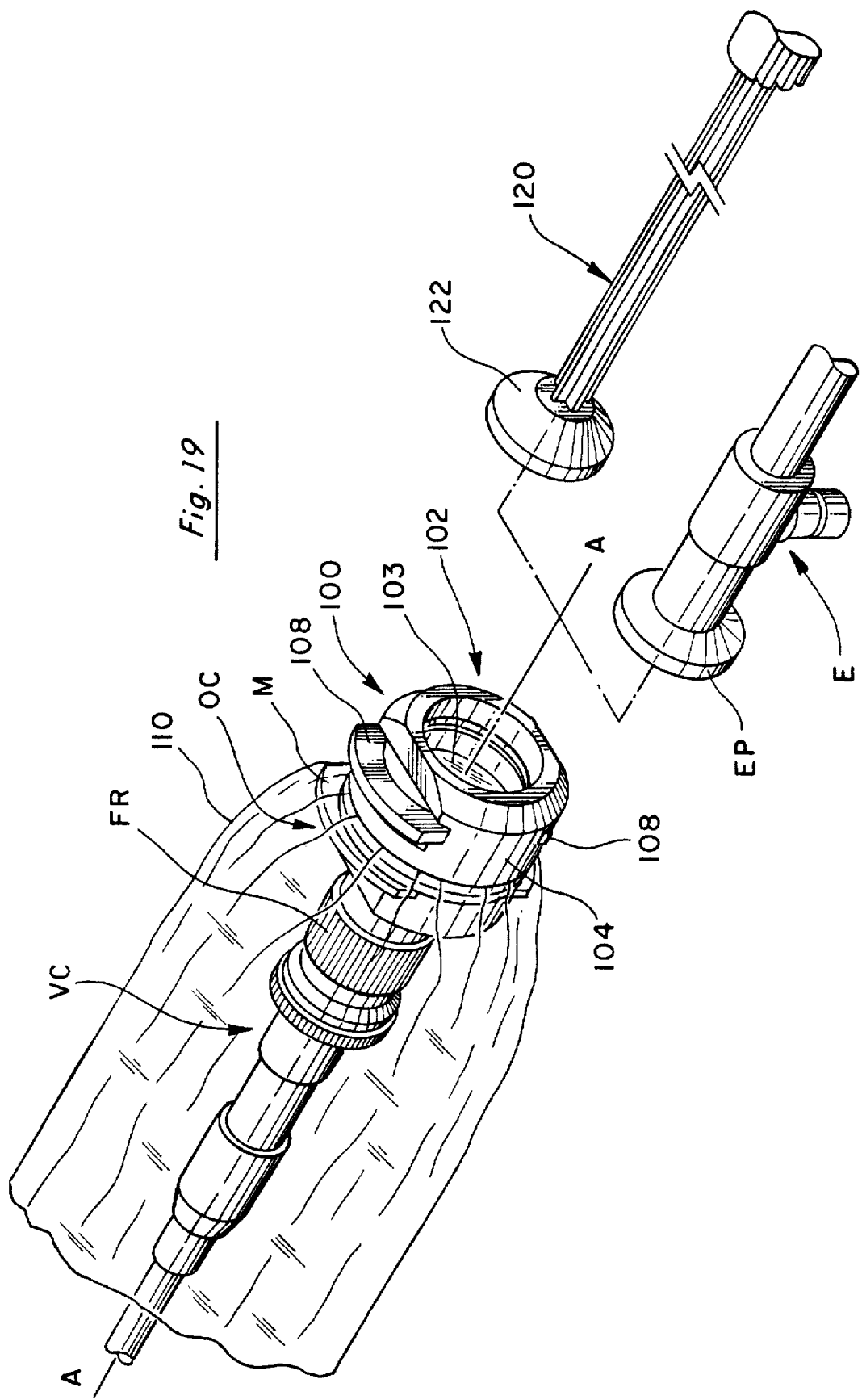
FIG. 19 is another perspective view of the fourth preferred embodiment, as shown in FIG. 18, illustrating the drape being pulled back over the first end of the coupler and wherein the sterile disposable wand is separated from the second end of the coupler so that the endoscope may then be connected thereto.

According to another novel aspect of this invention, a sterile disposable wand or stick 120 may initially be engaged with sterile couplers 10, 50, 70 or 100 to help stablize the sterile coupler and drape when the unsterile camera setup is connected to the sterile coupler. The sterile disposable wand 120 is shown in FIGS. 18 and 19. After engaging the unsterile camera setup with the coupler, the drape is pulled back over the camera, optical connector and trailing cables. The disposable wand 120 is then disengaged from the second end of the sterile coupler. As illustrated, the distal end of wand 120 includes an eyepiece portion 122 resembling the eyepiece of an endoscope. This configuration of eyepiece portion 122 enables the wand 120 to easily be engaged by the sliding quick releases 58, 81 and 108 of the second, third and fourth embodiments, respectfully. Alternatively, the distal end of wand 120 may simply be of a cylindrical shape to engage with the cylindrical interior wall 20 of the first embodiment.

When packaged prior to use, the sterile disposable wand 120 is pre-inserted into the second end of the coupler so that upon opening the packaged contents, the wand may be grasped by a sterile nurse who assists in stablizing the connection of the unsterile camera setup to the first end of the coupler.

Although the preferred embodiments disclosed herein illustrate the optical connector OC disposed within the drape, it is also within the spirit and scope of this invention to provide a coupler which is attachable to an optical connector positioned exteriorly of the drape. That is, some optical connectors are available which are autoclavable and thus can be made completely sterile. Thus, a particular surgeon may desire to focus an image onto the video camera by manipulating the focus ring exteriorly of the drape. For example, for the second embodiment shown in FIG. 11, the optical connector OC with focusing ring FR could be directly attached to the coupler 50, and a modified locking ring (not shown) could be used to connect the video camera VC to the optical connector OC which is placed exteriorly of the drape 60. Thus, an airtight and fluid-proof seal would be created between the video camera VC and the optical connector OC.

With this apparatus and method, a standard surgical camera and optical connector can be used which does not need to be sterilized through heating, soaking, or other sterilizing procedures and in which a number of endoscopes may be used with the same camera setup. The advantages of sterility and interchangeability of endoscopes makes this invention attractive to medical clinics and hospitals who often times cannot afford other endoscopic systems which, in order to maintain sterility, are much more complex and more difficult to use.

As discussed above in the prior art, an endoscope is typically attached to the optical connector which meant that in order for an endoscope to be placed in use, the sterile eyepiece of the endoscope had to be inserted within the drape and then directly attached to the unsterile optical connector. During this process, contamination is allowed to freely travel from the inside of the drape where the unsterile camera and optical connector are positioned, to the outside sterile environment of the operating room by means of the hole located in the distal end of the drape. Thus, according to the device and method of the invention disclosed herein, by isolating the first end of the coupler within the drape when the drape is extended for use over the unsterile camera, optical connector, and trailing cables, sterility may be maintained when subsequently attaching the endoscope to the coupler and for subsequent acts of changing endoscopes with the same camera setup.

This invention has been described in detail with reference to a particular embodiment thereof, but it will be understood that various other modifications can be affected within the spirit and scope of the invention.

I claim:

1. An apparatus for optically coupling a sterile endoscope to a sterile camera setup including an unsterile optical connector mounted to an unsterile camera having trailing cables, and for enclosing the unsterile camera setup in a sterile enclosure for use of the unsterile camera setup in a sterile surgical environment, said apparatus comprising:

a sterile coupler having a first end including a first mounting structure for connection to the unsterile optical connector, and having a second end including a second mounting structure for connection to the sterile endoscope, said sterile coupler further having an optical path positioned between said first and second ends thereof through which an image may be transmitted from the sterile endoscope to the unsterile camera;

a sterile barrier positionable between said first and second ends of said sterile coupler;

a sterile drape having an open distal end and including a drape ring formed thereon, said sterile drape positionable over said first end of said coupler and having a proximal end extendable over the unsterile optical connector, the unsterile camera and its trailing cables; and means for sealing said distal end of said drape between said first and second ends of said sterile coupler whereby said first end of said coupler is isolated from the sterile surgical environment located outside said drape said sealing means including a locking ring positionable between said first end and said second end of said sterile coupler and engaging said drape ring to compress the drape ring between said locking ring and said coupler.

2. An apparatus, as claimed in claim 1, wherein said optical path includes:

an interior passageway formed within said sterile coupler extending from said first end to said second end thereof.

3. An apparatus, as claimed in claim 1, wherein said sterile barrier includes:

an optically clear window mounted transversely in said optical path.

4. An apparatus, as claimed in claim 1, wherein said second mounting structure includes:

an interior passageway for receiving the sterile endoscope; and securing means attached to said second mounting structure for releasably attaching said second mounting structure to the sterile endoscope.

5. An apparatus, as claimed in claim 4, wherein said securing means includes a sliding quick release.

6. An apparatus, as claimed in claim 1, wherein said second mounting structure includes:

a transversely mounted securing means for releasably attaching said second mounting structure to the sterile endoscope.

7. An apparatus, as claimed in claim 1, wherein said sterile coupler further includes:

an integral engagement flange; and said drape ring being attached at said distal end of said drape for releasable engagement with said engagement flange and said locking ring.

8. An apparatus, as claimed in claim 1, wherein said locking ring further includes:

a spring washer attached to one side of said locking ring for providing an airtight and liquid proof seal between said optical connector and said sterile coupler.

9. An apparatus, as claimed in claim 1, further including:

a sterile disposable wand attachable to said second end of said sterile coupler for providing support to the camera setup when being attached to said sterile coupler.

10. An apparatus for coupling a sterile endoscope to an unsterile camera setup including an unsterile optical connector and an unsterile camera wherein the optical connector and camera are shielded from a sterile surgical environment, said apparatus comprising:

means for coupling the unsterile optical connector and camera to the sterile endoscope, said coupling means including a first end for connection to the unsterile optical connector and a second end for connection to the sterile endoscope;

an optical passageway extending from said first end of said coupling means to said second end of said coupling means enabling an image to be transmitted from the sterile endoscope to the unsterile camera;

means positionable between said first and second ends of said coupling means for providing an optically clear sterile barrier therebetween;

a sterile drape having an open distal end and including a drape ring formed thereon said sterile drape being positionable over said first end of said coupler and having a proximal end extendable over the unsterile camera setup; and means for sealing said open distal end of said sterile drape to said coupling means between said first and second ends thereof to form a fluid and airtight seal said sealing means including a locking ring positionable between said first end and said second end of said coupling means and engaging said drape ring to compress the drape between said locking ring and said coupling means.

11. An apparatus, as claimed in claim 10, wherein:

said optical passageway comprises an interior passageway formed within said coupling means extending from said first end to said second end thereof.

12. An apparatus, as claimed in claim 10, wherein said second end of said coupling means includes:

an interior passageway for receiving the sterile endoscope; and securing means attached to said second end of said coupling means for releasably attaching said second end to the sterile endoscope.

13. An apparatus, as claimed in claim 10, wherein said second end of said coupling means further includes:

a transversely mounted securing means for releasably attaching said second end of said coupling means to the sterile endoscope.

14. An apparatus, as claimed in claim 10, wherein:

said coupling means further includes an engagement flange; and said drape ring being positioned at said distal end of said drape for releasable engagement with said engagement flange and said locking ring.

15. An apparatus, as claimed in claim 10, wherein said coupling means includes:

an optical coupler mounting integral with said first end of said coupling means, and an endoscope mounting integral with said second end of said coupling means, said optical coupler mounting being slidably engageable with said endoscope mounting to releasably secure said distal end of said drape between said first and second ends of said coupling means.

16. An apparatus, as claimed in claim 10, further including:

a sterile disposable wand attachable to said second end of said coupling means prior to attaching the sterile endoscope to said second end of said coupling means, said sterile disposable wand providing support to the camera setup when being attached to said first end of said coupling means.

17. A method of coupling an unsterile camera setup including an optical connector and camera to a sterile endoscope wherein differing endoscopes may be freely interchanged without compromising the sterility of a surgical environment, said method comprising the steps of:

providing a sterile coupler having a first end attachable to the unsterile camera setup and a second end attachable to the sterile endoscope;

providing a sterile drape having an open distal end including a drape ring formed thereon positionable over the first end of the coupler and having a proximal end extendable over the camera setup;

sealing the distal end of the drape around the first end of the coupler by a locking ring engageable with said drape ring and said coupler thereby providing a sterile seal wherein the first end of the coupler is sealed within the drape and the second end of the coupler is exposed to the sterile surgical environment;

inserting the unsterile optical connector mounted to the unsterile camera within the proximal end of the drape;

attaching the unsterile optical connector to the first end of the coupler; and attaching the sterile endoscope to the second end of the coupler.

18. A method, as claimed in claim 17, further including the step of:

supporting the sterile coupler with a sterile disposable wand attached to the second end thereof prior to attaching the unsterile optical connector to the first end of the coupler; and detaching the sterile disposable wand from the second end of the sterile coupler prior to attaching the sterile endoscope to the second end of the coupler.

19. A method of coupling an unsterile camera setup to a sterile endoscope wherein sterility is maintained and wherein differing endoscopes may be freely interchanged without compromising the sterility of a surgical environment, said method comprising the steps of:

providing a sterile coupler having a first end releasably attachable to the unsterile camera setup and a second end releasably attachable to the sterile endoscope;

providing a sterile drape having an open end including a drape ring formed thereon positionable between the ends of the sterile coupler wherein the drape provides a first sterile barrier between exterior portions of the ends of the sterile coupler;

sealing the open end of the sterile drape between the ends of the sterile coupler by a locking ring engageable with said drape ring and said coupler;

providing a clear optical pathway within the sterile coupler wherein an image may be transmitted from the endoscope to the camera setup;

providing a window positionable within the sterile coupler along said optical pathway wherein a second sterile barrier is created between the interiors of the first and second ends of the sterile coupler;

attaching the first end of the sterile coupler to the camera setup; and attaching the second end of the sterile coupler to the sterile endoscope.

20. A method, as claimed in claim 19, including the further step of:

supporting the sterile coupler with a sterile disposable wand attached to the second end thereof prior to attaching the first end of the sterile coupler to the camera setup; and detaching the sterile disposable wand from the second end of the sterile coupler prior to attaching the second end of the sterile coupler to the sterile endoscope.

21. An apparatus for optically coupling a sterile endoscope to a sterile camera setup including an unsterile optical connector mounted to an unsterile camera having trailing cables, and for enclosing the unsterile camera setup in a sterile enclosure for use of the unsterile camera setup in a sterile surgical environment, said apparatus comprising:

a sterile coupler having a first end including a first mounting structure for connection to the unsterile optical connector, and having a second end including a second mounting structure for connection to the sterile endoscope, said sterile coupler further having an optical path positioned between said first and second ends thereof through which an image may be transmitted from the sterile endoscope to the unsterile camera;

a sterile barrier positionable between said first and second ends of said sterile coupler;

a sterile drape having an open distal end positionable over said first end of said coupler and having a proximal end extendable over the unsterile optical connector, the unsterile camera and its trailing cables;

means for sealing said distal end of said drape between said first and second ends of said sterile coupler whereby said first end of said coupler is isolated from the sterile surgical environment located outside said drape; and said first mounting structure includes an optical coupler part having an internal threaded portion, and said second mounting structure includes an endoscope coupler part having external threads for engaging said internal threaded portion to releasably secure said distal end of said drape therebetween.

22. An apparatus, as claimed in claim 21, wherein said sealing means includes:

a locking ring positionable between said optical coupler part and said endoscope coupler part.

23. An apparatus for optically coupling a sterile endoscope to a sterile camera setup including an unsterile optical connector mounted to an unsterile camera having trailing cables, and for enclosing the unsterile camera setup in a sterile enclosure for use of the unsterile camera setup in a sterile surgical environment, said apparatus comprising:

a sterile coupler having a first end including a first mounting structure for connection to the unsterile optical connector, and having a second end including a second mounting structure for connection to the sterile endoscope, said sterile coupler further having an optical path positioned between said first and second ends thereof through which an image may be transmitted from the sterile endoscope to the unsterile camera;

a sterile barrier positionable between said first and second ends of said sterile coupler;

a sterile drape having an open distal end positionable over said first end of said coupler and having a proximal end extendable over the unsterile optical connector, the unsterile camera and its trailing cables;

means for sealing said distal end of said drape between said first and second ends of said sterile coupler whereby said first end of said coupler is isolated from the sterile surgical environment located outside said drape; and said first mounting structure includes an optical coupler mounting and an interior passageway formed through said optical coupler mounting; and said second mounting structure includes an endoscope mounting having an annular flange for slidably engaging with said interior passageway to releasably secure said distal end of said drape between said optical coupler mounting and said endoscope mounting.

24. An apparatus for coupling a sterile endoscope to an unsterile camera setup including an unsterile optical connector and an unsterile camera wherein the optical connector and camera are shielded from a sterile surgical environment, said apparatus comprising:

means for coupling the unsterile optical connector and camera to the sterile endoscope, said coupling means including a first end for connection to the unsterile optical connector and a second end for connection to the sterile endoscope;

an optical passageway extending from said first end of said coupling means to said second end of said coupling means enabling an image to be transmitted from the sterile endoscope to the unsterile camera;

means positionable between said first and second ends of said coupling means for providing an optically clear sterile barrier therebetween;

a sterile drape having an open distal end being positionable over said first end of said coupler and having a proximal end extendable over the unsterile camera setup;

means for sealing said open distal end of said sterile drape to said coupling means between said first and second ends thereof to form a fluid and airtight seal; and an optical coupler part integral with said first end of said coupling means, and an endoscope coupler part integral with said second end of said coupling means, said optical coupler part being attachable to said endoscope coupler part by a threaded connection to releasably secure said distal end of said drape between said first and second ends of said coupling means.

* * * * *